United States Patent [19]

Huffman

[11] Patent Number: 4,573,964
[45] Date of Patent: Mar. 4, 1986

[54] OUTER TAMPON TUBE WITH RECESSED FINGER GRIP

[75] Inventor: Dawn M. Huffman, Winnebago County, Wis.

[73] Assignee: Kimberly-Clark Corporation, Neenah, Wis.

[21] Appl. No.: 542,864

[22] Filed: Oct. 17, 1983

[51] Int. Cl.⁴ .............................................. A61F 13/20
[52] U.S. Cl. ........................................ 604/15; 604/11
[58] Field of Search ..................................... 604/11–18

[56] References Cited

U.S. PATENT DOCUMENTS 3,884,233  5/1975  Summey ................................ 604/15
4,198,978  4/1980  Nigro ..................................... 604/15

Primary Examiner—C. Fred Rosenbaum
Assistant Examiner—Sherri E. Vinyard
Attorney, Agent, or Firm—J. P. O'Shaughnessy; J. J. Duggan

[57] ABSTRACT

This invention relates to a tampon tube in which the finger grip area has been cut through and compressed to provide an area of reduced diameter.

10 Claims, 7 Drawing Figures

OUTER TAMPON TUBE WITH RECESSED FINGER GRIP

FIELD OF THE INVENTION

This invention relates to tampon tubes and particularly outer tubes with finger gripping areas provided.

BACKGROUND OF THE INVENTION

Tampons, particularly so-called tube tampons, have recently become an important segment in the sanitary protection market. These tube tampons are bullet shaped and inserted by means of two tubes which telescope with respect to each other. The inner or plunger tube abuts the flat bottom of the tampon and is used to expel the tampon through the leading or insertion end of the outer tampon tube. This leading end may be open or may have some closure which is generally petal shaped and slit so that when force is applied the petals will be pushed outward and away from the leading edge of the tampon as it is expelled. The outer tampon tubes have an area at the opposite end for gripping so that the user braces two fingers against this finger gripping area of the outer tube while exerting pressure against the end of the inner tube opposite the tampon abutment end to begin and complete the expulsion and insertion process. Various means for forming this finger grip on the outer tube have been provided including rings of increased circumference and necked-in finger gripping portions as shown for example in U.S. Pat. No. 3,409,011. Outer tubes with necked in finger gripping portions are apparently the most satisfactory in performance.

Both inner and outer tampon tubes are made of either molded thermoplastic material, cardboard or cardboard like products. When outer tampon tubes are made with a necked-in portion regardless of whether the tubes are made from thermoplastic material or cardboard, is difficult to provide uniform inner and outer diameter in the necked-in tube portion. This nonuniform wall thickness is unsightly at the external wall portions of the tube. More importantly, however, the uneven inner wall profile resulting from this compression is likely to inhibit the expulsion function because of the uneven profile abutting the inner tube. In other words, the inner tube may not travel axially as expulsion occurs therefore distorting the direction of the expulsion force as applied to the bottom of the tampon making it difficult to remove from the outer tube. It will also enhance the possibility for improper directional insertion within the vagina.

SUMMARY OF THE INVENTION

According to this invention, an outer tampon tube is provided with a necked-in finger grip portion formed by the aid of a plurality of circumferentially spaced slits in the finger gripping area. By forming a necked-in portion by compressing after slitting, a uniform inner and outer profile of the outer tube is formed which substantially overcomes the difficulties inherent in the mere compression forming of the reduced diameter finger grip area.

DETAILED DESCRIPTION OF THE INVENTION AND DRAWINGS

The invention may be more readily understood with reference to the drawings in which.

Figure 1:
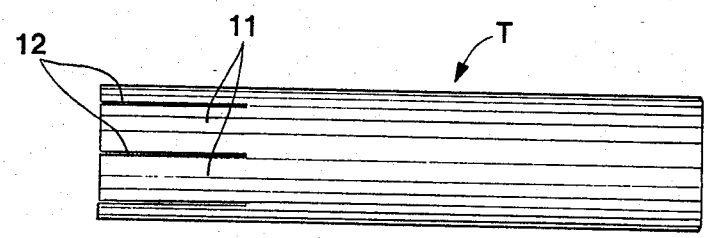
FIG. 1 is a side view of one embodiment of the tampon tube blank cut according to the teachings of this invention.

As can be seen from FIG. 1 the standard tube is provided with a plurality of essentially equally spaced slits 12 extending around the periphery of the portion of the outer tampon tube blank which will subsequently form the finger gripping portion. The spaced slits 12 form a series of sections 11 positioned between the slits.

Figure 2:
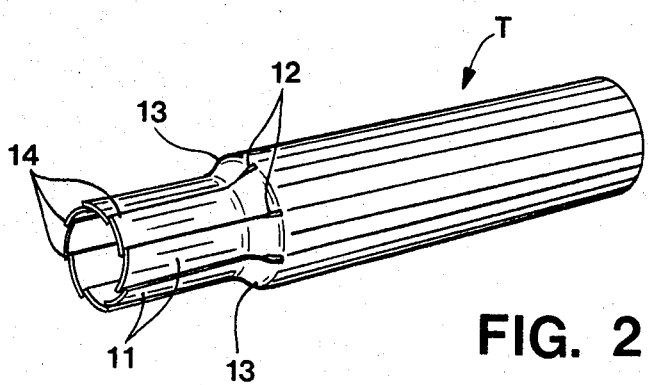
FIG. 2 is an end perspective view of an embodiment formed from the tampon finger gripping portion of FIG. 1.

In one embodiment of this invention the slit area is compressed to form a shoulder 13 as can be seen in FIG. 2 along with overlapped portions 14 of segments 11 so that there is sequential overlapping around the periphery of the finger gripping portion of tampon tube T.

Figure 3:
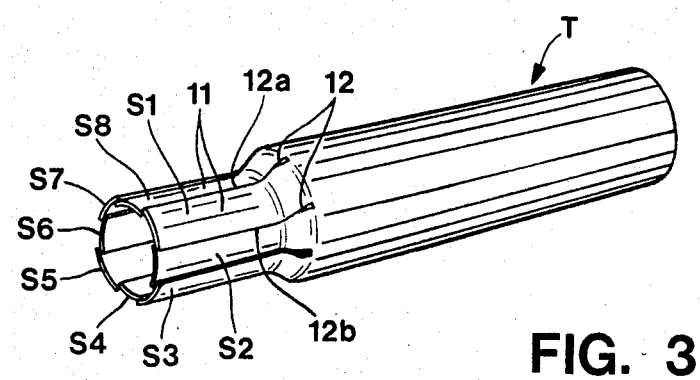
FIG. 3 is an end perspective view of another embodiment of the invention formed from the finger gripping portion of FIG. 1.

Alternatively, the segments 11 may be raised alternatively showing profile edges 12a and 12b as can be seen by reference to FIG. 3. The segments 11 are alternately raised and lowered so that segments S1, S3, S5, and S7 are totally above accompanying segments S2, S4, S6, and S8 as shown in FIG. 3. As can be seen in FIGS. 2 and 3, a substantially identical surface profile on the internal and external walls of the finger grip portion is produced by these particular embodiments.

Figure 4:
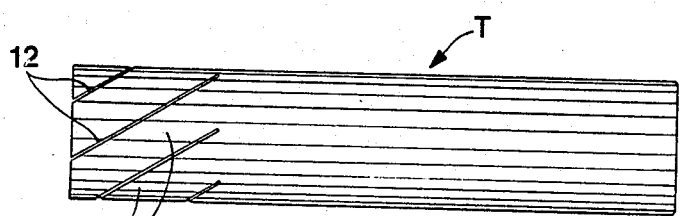
FIG. 4 is a second tampon tube blank.
Figure 5:
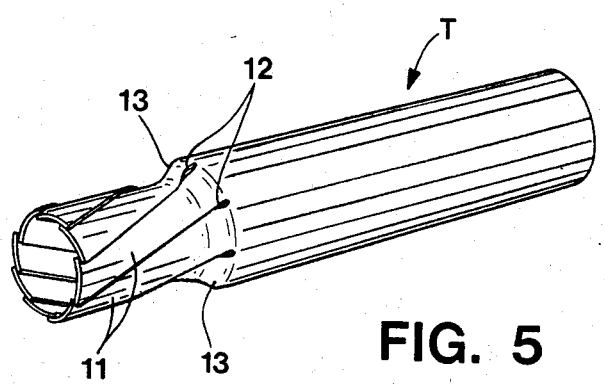
FIG. 5 is an end perspective view of an embodiment of the necked-in finger gripping portion of FIG. 4.
Figure 6:
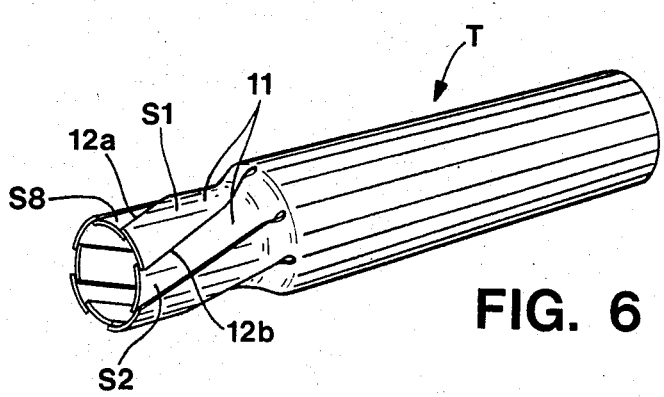
FIG. 6 is an end perspective view of a necked-in finger gripping portion formed from the blank of FIG. 4.

Other embodiments made according to this invention are based upon the tube blank shown at FIG. 4 having bias cut slits 12 extending around the periphery of the tube which is to become the finger gripping portion. As was the case with longitudinal cuts, the compressed bias cut finger gripping portion can have the individual segments 11 can be indexed and overlapped so that each segment is resting upon a portion of one adjacent segment while a second adjacent segment is positioned upon it. As shown in FIG. 5, or as shown in FIG. 6, a series of alternating segments 11 can be raised to rest upon the segments adjacent it on either side so that segment S1 is positioned totally above adjacent segments S2 and S8 as described more fully with respect to FIG. 3.

Figure 7:
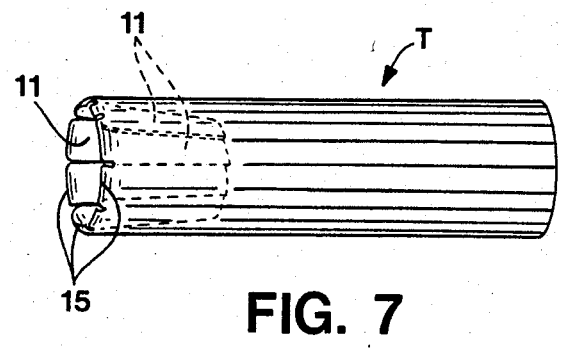
FIG. 7 is an end view of another embodiment of this invention.

FIG. 7 shows yet another alternative in which an indexed overlapped finger gripping portion such as shown in FIG. 2 is folded inward upon itself to form a folded bottom profile 15. This series of inward folded segments 11 tend to have a bias spring-like effect and act to maintain the inner tampon tube in a consistent axial position. The inward fold can be accomplished with any of the embodiments depicted in FIGS. 2, 3, 5 and 6 with the same inwardly directed biasing effect.

Another variant on the embodiment depicted at FIG. 7 is to merely push the end of the finger gripping portion upward to form a shoulder instead of folding the portion inward upon itself.

It is of course essential that the segments 11 be susbstantially equal in size and this is accomplished by spacing the slits at substantially equal distances during the forming of the tampon tube blank when the tube is circular. An elliptical cross sectional configuration is also possible utilizing the concepts of this invention and when an elliptical outer tube is used the slits 12 will not be evenly spaced. Generally, the number of segments varies between 5 and 8 depending upon the overall diameter of the tube and the preferred diameter of the necked-in portion desired.

The opposite end of the outer tampon tube may be either completely open or may have some type of petal shape or other closure which is opened during tube expulsion. These various configurations for the insertion-expulsion and are well known in the art and not part of this invention.

What is claimed is:

1. An elongated outer tampon tube formed from a single tubular element, said outer tampon tube having a longitudinal axis and two ends, with an insertion portion at one end and a gripping portion at the other end, said gripping portion being recessed with an outside diameter that is smaller than the outside diameter of said insertion portion, said recessed gripping portion being comprised of a plurality of overlapped elongated sections formed on said single tubular element by a plurality of slits through said tubular element, said slits being spaced around the circumference of said tubular element and extending generally longitudinally along said tubular element from the gripping portion end to a point spaced inwardly from that end.

2. The outer tampon tube according to claim 1 wherein there are between 5 and 8 slits in said gripping portion.

3. The outer tampon tube according to claim 1 wherein said sections are indexed and overlapped.

4. The outer tampon tube according to claim 1, 2, or 3 wherein said slits are parallel to the longitudinal axis of said outer tampon tube.

5. The outer tampon tube according to claim 1, 2, or 3 wherein the slits are on a bias with respect to the longitudinal axis of said outer tampon tube.

6. The outer tampon tube according to claims 1, 2, or 3 wherein said overlapped sections are folded inside said single tubular element.

7. An elongated outer tampon tube formed from a single tubular element, said outer tampon tube having a longitudinal axis and two ends, with an insertion portion at one end which receives a tampon therein, and a gripping portion at the other end which receives a tampon expulsion plunger therein, said gripping portion being recessed with an outside diameter that is smaller than the outside diameter of said insertion portion, said recessed gripping portion formed by a plurlity of slits through said tubular element which are regularly spaced around the circumference of said tubular element and extend generally longitudinally along said tubular element from the gripping portion end to a point spaced inwardly from that end, said slits defining a plurality of elongated sections which are overlapped to form said recessed portion.

8. A single tubular element for use in forming an outer tampon tube, said tubular element being elongated with a longitudinal axis and two ends, a portion of said tubular element having a plurality of slits formed therethrough which are spaced around the circumference of said tubular element and extend generally longitudinally along said tubular element from one of said tubular element ends to a point spaced inwardly therefrom, said slits forming a plurality of elongated sections which are overlapped in formation of the tampon outer tube to provide a reduced diameter gripping portion for the outer tampon tube.

9. The tubular element of claim 8 wherein the slits are parallel to said longitudinal axis of said tubular element.

10. The tubular element of claim 8 wherein the slits are on a bias with respect to said longitudinal axis of said tubular element.

* * * * *

UNITED STATES PATENT AND TRADEMARK OFFICE
CERTIFICATE OF CORRECTION

PATENT NO. : 4,573,964
DATED : March 4, 1986
INVENTOR(S) : Huffman

It is certified that error appears in the above-identified patent and that said Letters Patent are hereby corrected as shown below:

Column 3 Line 6, Numbers "5" and "8" should not be in bold type.

Column 4, Line 15, "plurlity" should read "plurality".

Signed and Sealed this

Thirty-first Day of March, 1987

*Attest:*

DONALD J. QUIGG

*Attesting Officer*     *Commissioner of Patents and Trademarks*